United States Patent [19]

Ledley et al.

[11] Patent Number: 4,478,816

[45] Date of Patent: Oct. 23, 1984

[54] RARE EARTH/CHELATING AGENT COMPLEX FOR DIGITAL FLUOROSCOPY

[75] Inventors: Robert S. Ledley, Silver Spring, Md.; Edward J. Zapolski, Arlington, Va.

[73] Assignee: Georgetown University, Washington, D.C.

[21] Appl. No.: 385,727

[22] Filed: Jun. 7, 1982

[51] Int. Cl.³ .............................................. A61K 49/04
[52] U.S. Cl. ......................................................... 424/4
[58] Field of Search ............................................. 424/4

[56] References Cited

U.S. PATENT DOCUMENTS

| | | | |
|---|---|---|---|
| 3,480,715 | 11/1969 | Catsch | 424/289 |
| 3,663,688 | 5/1972 | Grotenhuis | 424/1 |
| 3,995,020 | 11/1976 | Dandamudi | 424/1.5 |
| 4,017,596 | 4/1977 | Loberg et al. | 424/1 |
| 4,176,173 | 11/1979 | Winchell et al. | 424/5 |
| 4,192,859 | 3/1980 | Mackaness et al. | 424/5 |
| 4,283,382 | 8/1981 | Frank et al. | 424/8 |
| 4,310,507 | 1/1982 | Luckey | 424/4 |

*Primary Examiner*—Frederick E. Waddell
*Attorney, Agent, or Firm*—Oblon, Fisher, Spivak, McClelland & Maier

[57] ABSTRACT

A rare earth/chelating agent complex is employed in digital fluoroscopy. More specifically, a contrast medium is utilized in digital fluoroscopy, the contrast medium consisting of a non-radioactive composition of a rare earth metal and a chelating agent. The rare earth metal is lutecium or ytterbium, while the chelating agent is DTPA, EHPG or HBED. The digital fluoroscopy method results in the development of diagnostic energy difference image information as a result of application of X-ray beams of two different energy levels, coupled with subtraction processing of the resulting image information.

6 Claims, 4 Drawing Figures

DTPA

EHPG

HBED

RARE EARTH/CHELATING AGENT COMPLEX FOR DIGITAL FLUOROSCOPY

BACKGROUND OF THE INVENTION

1. Field of the Invention

The invention generally relates to the use of a rare earth/chelating agent complex for digital fluoroscopy, and more particularly to the use, in digital fluoroscopy, of a contrast medium consisting of a non-radioactive composition of a rare earth metal and a chelating agent.

2. Description of Prior Art

Digital fluoroscopy or digital fluorography (DF) is a technique whereby X-ray signals are detected electro-optically and converted into digital forms which can be processed, recorded and displayed. Processing provides a means to remove certain features from the image and enhance other clinically significant structures.

For the diagnosis of vascular diseases, this can be accomplished either by temporal subtraction wherein two images are obtained before and some time after administration of vascular contrasting media and then subtracted, or by energy subtraction wherein images are nearly simultaneously acquired using different energy X-rays, or by a hybrid technique embodying both temporal and energy subtraction processes.

The field of DF is described by a number of synonymous terms including digital radiography, digital subtraction fluoroscopy, computerized fluoroscopy, digital video angiography, digital video subtraction angiography, digital subtraction arteriography, and intravenous video arteriography. DF provides a simpler means for diagnosis of vascular diseases with less patient risk than conventional arteriography or nuclear imaging techniques.

Current techniques of vascular imaging by DF procedures necessitate parenteral administration of large doses of diatrizoate meglumin or related iodinated substances as contrast media (18–30 gm of iodine per 30–50 ml injection), and the ultimate success or failure of the procedure is entirely dependent upon the absence of any patient motion during or between acquisition of the two images. In addition, injection of heavily iodinated contrast substances is associated with definite patient risk, and is accompanied by significant patient discomfort following the procedure.

There is an urgent need, therefore, not only to develop a less toxic contrast material, but also to develop a contrast media, and a method for employing it, that will improve current DF techniques so that patient motion is no longer a problem.

A digital radiography system essentially consists of an X-ray source, X-ray image intensifier, a high quality TV camera whose output is converted into digital format, a digital image processor, and a display. Such a system is disclosed in copending application Ser. No. 300,587 filed on Sept. 9, 1981.

The system provides for increased low contrast capability and shorter acquisition time, compared to conventional diagnostic radiology equipment. Processing systems provide for rapid image construction, and also for flexible options, such as subtraction, multiplication and convolution, that can be designed to increase the clinical potential of the technology.

Two promising processing techniques, temporal subtraction and energy subtraction (both discussed above), are presently being developed for contrast imaging. More attention has been devoted to temporal subtraction processing techniques, wherein images are obtained before and after administration of the contrasting agent, and these images are subtracted to remove underlying or overlying structures from the field of interest.

Iodine-containing compounds are the only type of contrast agent used in human vascular studies using DF. The greatest limitation to this processing method is that there is a finite, and sometimes prolonged, interval between the images obtained prior to and at the peak of contrast. Patient or physiologic movements between exposures occur, and the subtraction image obtained consequently suffers. The technique also requires administration of relatively high doses of contrast agent, which is frequently accompanied by some definite patient risk and discomfort.

SUMMARY OF THE INVENTION

It is in light of the above background that the present invention has been developed.

The invention generally relates to the use of a rare earth/chelating agent complex in digital fluoroscopy, and more particularly to the use of a contrast medium consisting of a non-radioactive composition of a rare earth metal and a chelating agent. The rare earth metal may be selected from the class consisting of lutetium and ytterbium, while the chelating agent may be selected from one of the following: diethylenetriamine pentaacetic acid; ethylene-diamine-N,N'-bis (2-hydroxy-phenylacetic acid); and N,N'-bis (2-hydroxbenzyl) ethylene-diamine-N,N'-diacetic acid. These will be referred to below as DTPA, EHPG and HBED, respectively.

The method or technique of the present invention generally relates to the use of the rare earth metal chelate complex as contrast agent for use with X-rays at two different energy levels in conjunction with digital fluoroscopy so as to preclude the occurrence of motion artifacts. It is to be noted that the present invention takes advantage of the existence of more sensitive instrumentation for detecting X-ray signals, or the absence of X-ray signals, so that a non-radioactive composition can be utilized.

Therefore, it is an object of the present invention to provide a rare earth/chelating agent complex for digital fluoroscopy.

It is an additional object of the present invention to provide a non-radioactive composition of a rare earth metal and a chelating agent for digital fluoroscopy.

It is an additional object of the present invention to provide a method or technique for utilizing a rare earth/chelating agent complex for digital fluoroscopy, wherein X-rays of two different energy levels thereof are employed.

The above and other objects that will hereinafter appear, and the nature of the invention, will be more clearly understood by reference to the following description, the appended claims, and the accompanying drawings.

DETAILED DESCRIPTION

Figure 1:
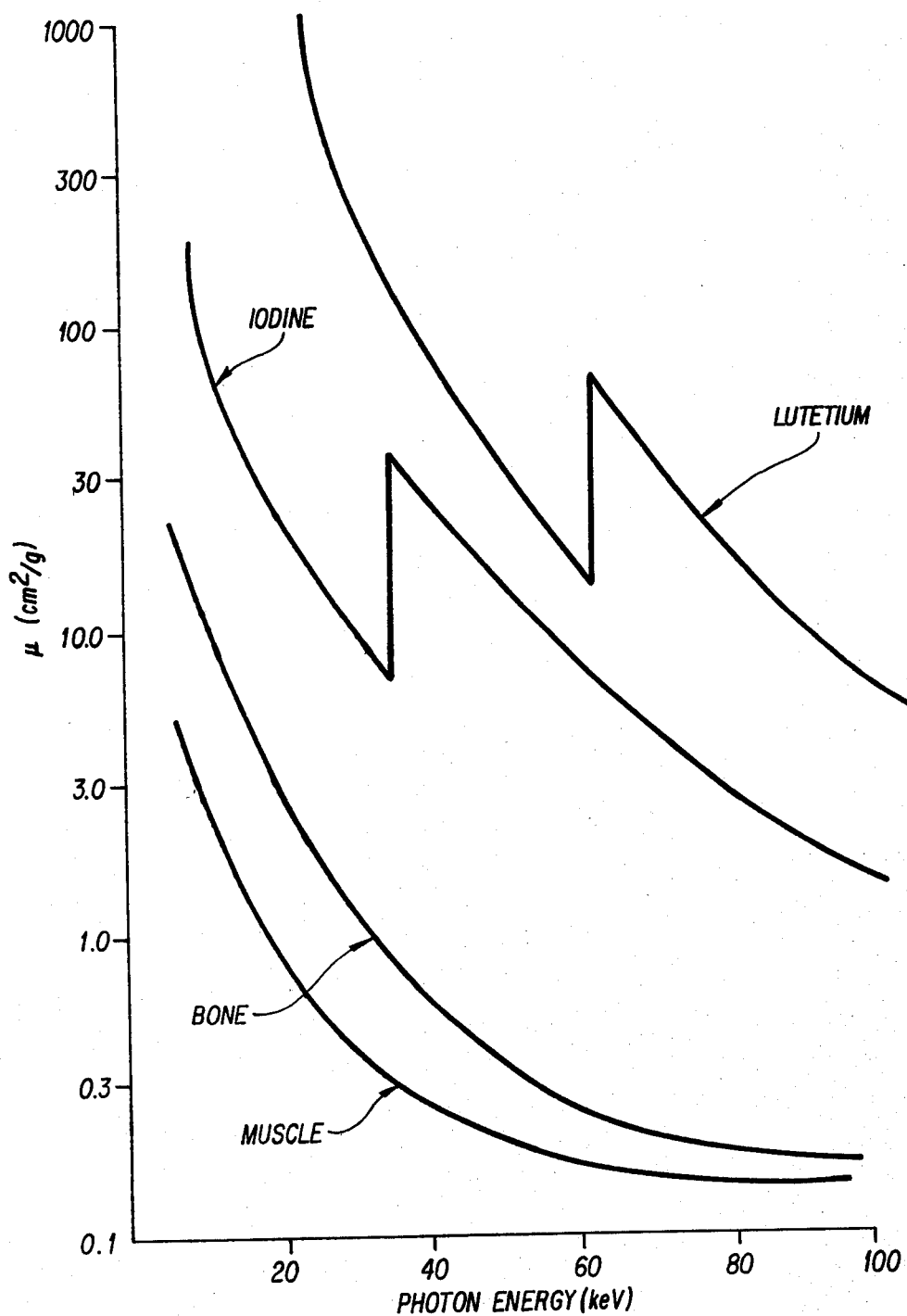
FIG. 1 is a graphical illustration of mass attenuation coefficient energy dependences for bone, muscle, iodine and lutetium, which illustrates that a lower dose of the inventive contrasting agent can be employed to obtain images at least as good as those obtained with iodinated substances.

The present invention will now be described in more detail with reference to the above figures.

As indicated above, the specific objective of the present invention relates to the development of a new contrast imaging agent(s) which can be used in vascular diagnostic studies by digital fluoroscopy. Ytterbium or lutetium DTPA or related chelates of rare earth elements (EHPG or HBED) are excellent candidate compounds in this respect. They are relatively non-toxic, and rapidly cleared from the blood stream and excreted in urine, and possess K-edge mass attenuation coefficient discontinuities at a high enough energy level (near 60 keV) to provide the capability of processing images by K-edge energy subtraction, and yet still utilize X-ray beams energetically suited for diagnostic radiography.

In energy subtraction processing, images are obtained nearly simultaneously from two X-ray beams of different energy and then subtracted to capitalize upon the greater attenuation difference for high Z elements (compared to soft tissue elements) for photons of high and lower energies. Complications arising from the inevitable motion can thus be minimized.

In theory, the greatest relative ratio of contrast (contrast iodine/soft tissue) will be attained when the energy of the X-ray beams straddles the large mass attenuation coefficient discontinuity at the K-edge. However, for all iodinated contrast agents of the prior art, consideration of excessive exposure to the patient and insufficient X-ray tube output intensity at low energy levels (near 33 kVp) negate utilization of the K-edge subtraction approach. When exposure beams are energetically higher than the iodine K-edge, as is the case in diagnostic radiology, subtraction processing still results in residual signals from non-iodinated substances such as bone. More particularly, at these higher energies, the differences in X-ray attenuation for iodine are not as great as those attained when working at or near the K-edge, so that the sensitivity for iodine detection is not improved. Consequently, only marginal reductions in the dose of this type of contrast agent, as administered to the patient, will be experienced, and the toxic and unpleasant effects upon the patient are not alleviated by such an approach.

The present invention results from the realization that the K-edge mass attenuation coefficient discontinuies for the rare earth elements ytterbium ($Z=70$) and lutetium ($Z=71$) are 61.3 and 63.3 keV, respectively. If these elements are used in a contrast compound, there is provided a means to apply energy subtraction processing with X-ray beams which will straddle the K-edge discontinuity and yet will be energetically within the range employed in routine diagnostic radiographic procedures. This approach results both in the loss of undesirable portions of the images, since the energy dependence of the attenuation coefficient for bone is not as pronounced near 60 keV, and in an increase in the contrast ratio (rare earth/tissue) so that a lower dose of contrasting agent can be employed to obtain images at least as good as those obtained with iodinated substances.

This is illustrated in FIG. 1, which is a graphical illustration of the mass attenuation coefficient energy dependence for bone, muscle, iodine and lutetium. As seen in FIG. 1, for lutetium, the difference in the mass attenuation coefficient between 60–70 kVp is large. On the other hand, although there is, for iodine at photon energies near 33 kVp, a difference of 25 $cm^2/g$, between 60 and 100 kVp, the difference is much smaller, only one-fifth as much.

It might be suggested that hybrid subtraction, a second-order technique that combines temporal and energy subtraction, can eliminate artifacts caused by motion. However, in this processing technique, iodine sensitivity is not enhanced and high dose requirements for contrasting agents remain, so that the improvement in image quality is still compromised by patient discomfort and risks due to the contrast media injected. Movement is still a problem.

Despite the favorable high energy k-edge mass attenuation coefficient discontinuity of rare earth elements, until the advent of the present invention, they have not been exploited for contrast studies. Rare earth salts are classified as only slightly toxic. More specifically, whereas neodymium salts (250–500 mg I.V.) have been used in anticoagulation therapy, given repeated injections of up to 12.5 mg/kg, toxic manifestations in humans have been noted. In contrast, chelated metals are considerably less toxic than are salts of that metal. In short, the present invention takes advantage of the remarkable ability of chelation to reduce the toxic effects of metals.

Figure 2A:
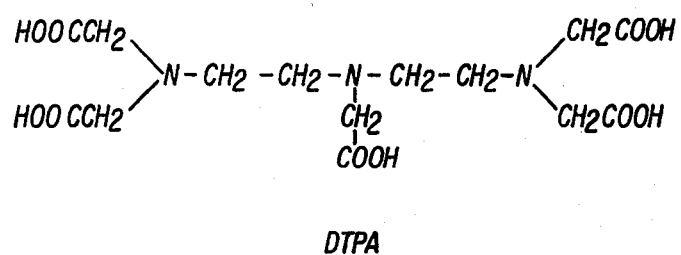
FIGS. 2A–2C are diagrams of the structures of the three chelating agents employed in accordance with the present invention.
Figure 2B:
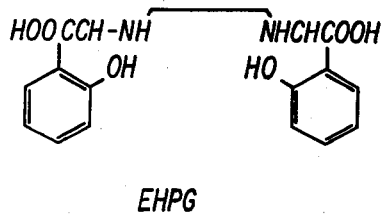
Figure 2C:
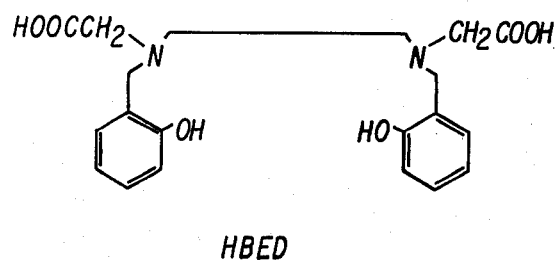

FIGS. 2A–2C are diagrams of the chelated structures for the various chelating agents (DTPA, EHPG and HBED) used in the rare earth/chelating agent complex for digital fluoroscopy, in accordance with the present invention.

It is to be noted that the relative in vivo stability of a metal chelate complex limits the concentration of a free metal ion when competing hydrolysis reactions are absent. Rare earth chelates of DTPA (shown in FIG. 2A) are extremely stable in this respect, with stability constants that approximate $10^{20}$ (K=[metal chelate]/[chelate ligand][metal ion]). At equal chelate/ligand concentrations, free metal ion concentration is in effect $10^{-20}$ M/L.

Other potentially useful and stronger chelate ligands exist. The chelators of FIGS. 2B and 2C contain phenolate ligands. Ferric chelates of EHPG and HBED exhibit stability constants of and $10^{33}$ and $10^{40}$. Corresponding values for Fe(III) DTPA complexes are $10^{28}$. If the same order of increased stability occurs between DTPA and EHPG, one anticipates rare-earth EHPG complex stability constants to be in the order of $10^{26}$.

Chelates of ytterbium or lutetium, by virtue of the low toxicity of the metal ion (and much lower toxicity as a chelate complex), confinement to extracellular fluids, relative biochemical inertness, and rapid biological clearance, are potentially useful vascular contrast imaging agents which can be detected at suitably low concentrations by K-edge dual energy subtraction processing via digital fluoroscopy, and offer material advantages over the conventional heavily iodinated contrasting substances currently in use. Since both images should be obtainable within fractions of a second of each other by the energy subtraction technique, problems due to motion are eliminated by this processing technique and yield highly detailed and clear radiographs for diagnosis.

The relatively low toxicity of all rare earth salts does not limit potential utilization of any member of the lanthanides as a possible contrasting element, with the exception of cerium, a strong redox reagent.

All rare earth chlorides are very water soluble (60-100 g/100 ml) and certain types of chelates are even more soluble. Preparation of the metal chelates is performed by simple metathesis. A solution of calcium chelate (or chelator) is mixed with a rare earth chloride solution and then neutralized. A molar excess of chelator is employed to assure that all metal ion is chelated, and calcium chelate is employed to insure that excess chelator will not sequester plasma calcium.

The selection of the ideal rare earth element for contrast use will be determined by its characteristic K-edge absorption line in relation to the two X-ray beams employed for dual energy image subtraction processing. If monoenergetic beams are to be employed, lutetium would be the element of choice. However, in diagnostic radiology, we do not deal with this type beam but rather with a spectrum of energy having a characteristic mean peak. This spectrum can be altered by manipulation of the X-ray tube accelerating voltage, or by filters. It is therfore conceivable that different rare earth metal chelate compounds will be best suited for use with different DF instruments.

By use of these two approaches (filtration and X-ray energy) two X-ray beams are obtainable, the peak energy of each beam being on the order of 50-65 keV, separated by 5-10 keV. For example, with a generating voltage of 75 kVp, a gadolinium filter (0.127mm) provides a photon beam with 68% of the energy being between 33-50 keV, 13% below, and 18% above. If higher Z elements such as holmium, erbium or thulium (K-edge absorption edges at 55.6, 57.5 and 59.4 keV, respectively) are employed as filter materials, the spectrum is shifted to a higher peak, upward and closer to the lutetium low energy K-edge minimum just below 63 keV. The unfiltered beam has the required higher energy peak output above 63 keV. The filters can be shifted into position automatically within fractions of a second.

In actual use, 25 mL of a sterile aqueous solution containing 5 gms of Lu DTPA and 1 gm of Ca DTPA is injected intravenously. Two images are obtained by digital fluorography within a fraction of a second of each other. One is acquired from an X-ray beam having a peak photon energy near 60 kVp, the other near 65 kVp. Subtraction processing then yields a diagnostic energy difference image that portrays the contrast agent in the vasculature.

While preferred forms and arrangements have been shown in illustrating the invention, it is to be clearly understood that various changes in detail and arrangement may be made without departing from the spirit and scope of this disclosure.

What is claimed is:

1. A method of obtaining diagnostic energy difference image information of a patient, comprising the steps of:
   (a) injecting a sterile aqueous solution comprising an effective amount of a non-radioactive rare earth metal and a chelating agent into the patient intraveneously;
   (b) applying an X-ray beam having a first energy level to the paitent to obtain first image information;
   (c) applying an X-ray beam having second energy level to the patient to obtain a second image information; and
   (d) subtraction processing the first and second image informations to obtain the diagnostic energy difference image information.

2. The method of claim 1, further comprising step (e) of displaying the energy difference image information.

3. The method of claim 1, wherein said rare earth metal is selected from the class consisting of lutetium and ytterbium.

4. The method of claim 1, wherein said chelating agent is diethylenetriamine pentaacetic acid.

5. The method of claim 1, wherein said chelating agent is ethylenediamine-N,N'-bis (2-hydroxy-phenylacetic acid).

6. The method of claim 1, wherein said chelating agent is N,N'-bis (2-hydroxbenzyl) ethylene-diamine-N,N'-diacetic acid.

* * * * *